United States Patent
Guitard et al.

(10) Patent No.: US 6,949,555 B2
(45) Date of Patent: Sep. 27, 2005

(54) USE OF ORGANIC COMPOUNDS

(75) Inventors: Christiane Guitard, Hégenheim (FR); Beate Müller, Hänner (DE); Rebecca Emmons, Riehen (CH)

(73) Assignee: Novartis AG, Basel (CH)

( * ) Notice: Subject to any disclaimer, the term of this patent is extended or adjusted under 35 U.S.C. 154(b) by 521 days.

(21) Appl. No.: 09/731,139

(22) Filed: Dec. 6, 2000

(65) Prior Publication Data

US 2001/0016586 A1 Aug. 23, 2001

(30) Foreign Application Priority Data

Dec. 23, 1999 (EP) .............................. 99125761

(51) Int. Cl.$^7$ ............................................ A61K 31/495
(52) U.S. Cl. ................... 514/255.06; 514/866
(58) Field of Search ........................... 514/255.06, 369, 514/635

(56) References Cited

FOREIGN PATENT DOCUMENTS

| WO | WO 98/56378 | 12/1998 |
|---|---|---|
| WO | WO 00/27434 | 5/2000 |
| WO | WO 00/28989 | 5/2000 |

OTHER PUBLICATIONS

Li et al., "Effect of metformin on impaired glucose tolerance (IGT) patients", Jiefangjun Yixue Zazhi (1999), 24(2), pp. 107–109 (see the enclosed abstract).*

Derwent Abstract 2000–03788, Dunning et al., "Nateglinide improves prandial glucose excursions by restoring early insulin secretion in pre–diabetic monkeys" (XP–002148734).

Derwent Abstract PREV 199900368837, Dunning et al. Mimicking cephalic insulin release with the rapid onset/short duratio insulinotrophic agent, nateglinide, reduces prandial glucose excursions without increasing total insulin exposure in IGT monkeys. (XP–002148735).

Sartor et al., Diabetes, vol. 29, pp. 41–49 (1980) (XP–000938566).

Page et al., Quarterly Journal of Medicine, vol. 86, pp. 145–154 (1993) (XP–000938433).

Melander, A. , Diabetic Medicine, vol. 13, pp. 143–147 (1996) (XP–000938428.

International Search Report.

* cited by examiner

*Primary Examiner*—Kevin E. Weddington
(74) *Attorney, Agent, or Firm*—Gregory D. Ferraro

(57) ABSTRACT

The invention relates to the use of a hypolipidemic agent or a pharmaceutically acceptable salt thereof for the manufacture of a medicament for the prevention or delay of the progression to overt diabetes, especially type 2, prevention or reduction of microvascular complications (eg, retinopathy, neurophathy, nephropathy), prevention or reduction of excessive cardiovascular morbidity (eg, myocardial infarction, arterial occlusive disease, atherosclerosis and stroke) and cardiovascular mortality, prevention of cancer and reduction of cancer deaths. Additionally, the invention relates to the use of a treatment for diseases and conditions that are associated with IGM, IGT or IFG.

5 Claims, No Drawings

USE OF ORGANIC COMPOUNDS

Impaired Glucose Metabolism (IGM) is defined by blood glucose levels that are above the normal range but are not high enough to meet the diagnostic criteria for type 2 diabetes mellitus. The incidence of IGM varies from country to country, but usually occurs 2–3 times more frequently than overt diabetes. Until recently, individuals with IGM were felt to be pre-diabetics, but data from several epidemiologic studies argue that subjects with IGM are heterogeneous with respect to their risk of diabetes and their risk of cardiovascular morbidity and mortality. The data suggest that subjects with IGM, in particular IGT, do not always develop diabetes, but whether they are diabetic or not, they are, nonetheless, at high risk for cardiovascular morbidity and mortality.

Among subjects with IGM, about 58% have Impaired Glucose Tolerance (IGT), another 29% have Impaired Fasting Glucose (IFG), and 13% have both abnormalities (IFG/IGT). IGT is characterized by elevated postprandial (post-meal) hyperglycemia while IFG has been defined by the ADA (see Table below) on the basis of fasting glycemic values.

The categories of Normal Glucose Tolerance (NGT), IGM and type 2 diabetes mellitus were defined by the ADA in 1997 as follows:

|  | NGT | IGM | Type 2 Diabetes mellitus |
|---|---|---|---|
|  |  | IFG |  |
| FPG level | <6.1 mmol/L (<110 mg/dl) And | 6.1–7 mmol/L (110–126 mg/dl) and/or | >7 mmol/L (>126 mg/dl) or |
|  |  | IGT |  |
| 2 h postprandial glucose level (75 g OGTT *) | <7.8 mmol/l (<140 mg/dl) | 7.8–11.1 mmol/L (140–220 mg/dl) | >11.1 mmol/L (>200 mg/dl) |

*)These criteria were defined using the WHO recommended conditions for administration of an oral glucose tolerance test (OGTT), i.e., the oral administration of a glucose load containing the equivalent of 75 g of anhydrous glucose dissolved in water with a blood sample taken 2 hours later to analyze the post-prandial glucose.
Other OGTT test conditions have confirmed the associated risks of the IGT and IFG categories including: 1) using 50 g glucose instead of 75 g, 2) using a casual (non-fasting) glucose sample as the analyte, and 3) analyzing the post-prandial glucose at 1 hour rather than 2 hours post-glucose load.
Under all of these conditions, the glycemic categories defined above have been linked to the increased risks described below, but the standardized OGTT is preferred in order to minimize variations in test results.

Individuals with IGM, especially those with the subcategory IFG, are known to have a significantly higher rate of progression to diabetes than normoglycemic individuals and are known to be high at cardiovascular risk, especially if they develop diabetes. Interestingly, subjects with IGM, more specifically those with the subcategory IGT, have a high incidence of cancer, cardiovascular diseases and mortality even if they never develop diabetes. Therefore, IGM and more specifically, the subgroup IFG, appears to be at high cardiovascular risk, especially after patients become overtly diabetic. IGT, on the other hand, is associated with a high risk for cancer, cardiovascular disease and mortality in nondiabetics and diabetics. The increased risk associated with IGT is independent of all other known cardiovascular risk factors including age, sex, hypertension, low HDL and high LDL cholesterol levels [Lancet 1999; 354: 617–621].

One mechanism through which IGM, and more specifically, IGT, has been linked to micro- and macroangiopathic complications in the absence of the abnormal FPG characteristic of diabetics, is postprandial hyperglycemia. Isolated postprandial hyperglycemia, even in nondiabetics, has been shown to reduce the natural free-radical trapping agents (TRAP) that are present in serum. Decreasing the level of TRAP has been shown, under experimental conditions, to be associated with an increase in free radical formation and increased oxidative stress. These free radicals have been implicated in the pathological microvascular and macrovascular changes associated with atherosclerosis, cardiovascular morbidity and mortality, and cancer [Ceriello, A, Diabetic Medicine 15: 188–193, 1998]. The decrease of natural antioxidants like TRAP during postprandial hyperglycemia may explain the increased cardiovascular risk in subjects with IGM, and specifically IGT, that do not develop diabetes. The fact that IGT is an independent risk factor in non-diabetics as well as diabetics justifies it as a new indication, separate from diabetes, for prevention and treatment of cardiovascular morbidity and mortality as well as cancer.

IGM is associated with following potential diseases or conditions: 1.) progression to overt diabetes mellitus type 2 (Code 250.2 of the International Classification of Diseases $9^{th}$ version=ICD-9 Code 250.2) [Diabetes Research and Clinical Practice 1998; 40: S1-S2]; 2.) increased microvascular complications of diabetes especially retinopathy and other ophthalmic complications of diabetes (ICD-9 code 250.5), nephropathy (ICD-9 code 250.4), neuropathy (ICD-9 code 250.6) [Diabetes Care 2000; 23: 1113–1118], and peripheral angiopathy or gangrene (ICD-9 code 250.7); 3.) increased cardiovascular morbidity (ICD-9 codes 410–414) especially myocardial infarctions (ICD-9 code 410), coronary heart disease or atherosclerosis (ICD-9 code 414) and other acute and subacute forms of coronary ischemia (ICD-9 code 411); 4.) excess cerebrovascular diseases like stroke (ICD-9 codes 430–438) [Circulation 1998; 98: 2513–2519]); 5.) increased cardiovascular mortality (ICD-9 codes 390–459) [Lancet 1999; 354: 617–621], and sudden death (ICD-9 code 798.1); 6.) higher incidences and mortality rates of malignant neoplasms (ICD-9 codes 140–208) [Am J Epidemiol. 1990; 131: 254–262, Diabetologia 1999; 42: 1050–1054]. Other metabolic disturbances that are associated with IGM include dyslipidemia (ICD-9 code 272), hyperuricemia (ICD-9 code 790.6) as well as hypertension (ICD-9 codes 401–404) and angina pectoris (ICD-9 code 413.9) [Ann Int Med 1998; 128: 524–533].

Clearly, the broad spectrum of diseases and conditions that are linked to IGM, and especially IGT, represents an area of tremendous medical need. Many of the same diseases and conditions have been associated with both IGM and diabetes, but only recently has it been possible to identify that that the nondiabetic population that has IGM, and especially IGT, should be an indication for prevention and treatment. Accordingly, in subjects with IGM and especially IGT and/or IFG, the restoration of early phase insulin secretion and/or the reduction of prandial hyperglycemia should help to prevent or delay the progression to overt diabetes and to prevent or reduce microvascular complications associated with diabetes by preventing the development of the overt diabetes. In addition, in individuals with IGM and especially those with IGT and/or IFG, the restoration of early phase insulin secretion and/or reduction of postprandial hyperglycemia should also prevent or reduce the excessive cardiovascular morbidity and mortality, and prevent cancer or reduce its mortality in individuals.

Thus the stage between normoglycemia and type 2 diabetes mellitus, especially the glycemic stage, is becoming of major interest and there is a strong need for a method to inhibit or delay the progression to type 2 diabetes mellitus, and also the variety of cardiovascular and microvascular conditions and diseases as well as cancer that have been associated with IGM and especially IFG and/or IGT.

It has unexpectedly been found that hypoglycemic agents such as insulin secretion enhancers can be used to prevent or delay the progression to overt diabetes, to reduce microvascular complications of diabetes, to reduce vascular, especially cardiovascular, mortality and morbidity, especially cardiovascular morbidity and mortality, and to reduce increased mortality related to cancer in individuals with IGT and/or IFG.

Hypoglycemic agents comprise, for example, an insulin secretion enhancer or an insulin sensitivity enhancer (insulin resistance deblocker) or insulin of, if appropriate, in each case a pharmaceutically acceptable salt thereof.

Insulin secretion enhancers are active ingredients that have the property to promote the secretion of insulin from pancreatic β-cells.

An insulin secretion enhancer (also called insulin secretogogue and insulinotropic agent) is, for example, a short-acting or a long-acting hypoglycemic agent.

A short-acting hypoglycemic is, for example, a phenylacetic acid derivative, furthermore gliquidone.

A corresponding phenylalanine derivative is, for example, nateglinide [N-(trans-4-isopropylcyclohexylcarbonyl)-D-phenylalanine] (cf. EP 196222 and EP 526171) of the formula

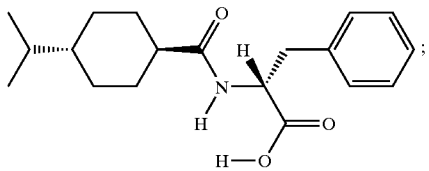

(I)

and repaglinide [(S)-2-ethoxy-4-{2-[[3-methyl-1-[2-(1-piperidinyl)phenyl]butyl]amino]-2-oxoethyl}benzoic acid]; and in free form or, if appropriate, in each case a pharmaceutically acceptable salt thereof.

The term nateglinide likewise comprises crystal modifications such as disclosed in EP 0526171 B1 or U.S. Pat. No. 5,488,510, respectively, the subject matter of which, especially with respect to the identification, manufacture and characterization of crystal modifications, is herewith incorporated by reference to this application, especially the subject matter of claims 8 to 10 of said U.S. patent (referring to H-form crystal modification) as well as the corresponding references to the B-type crystal modification in EP 196222 B1 the subject matter of which, especially with respect to the identification, manufacture and characterization of the B-form crystal modification. Preferably, in the present invention, the B- or H-type, more preferably the H-type, is used.

A longacting hypoglycemic is, for example, a biguanide derivative or a sulphonyl urea derivative.

An approriate biguanide is, for example, metformin or, if appropriate, a pharmaceutically acceptable salt thereof, especially the hydrochloride thereof.

Examples of sulfonylurea derivatives (SU) are, especially those which promote the secretion of insulin from pancreatic β-cells by transmitting signals of insulin secretion via SU receptors in the cell membrane, including (but are not limited to) tolbutamide; chlorpropamide; tolazamide; acetohexamide; 4-chloro-N-[(1-pyrolidinylamino)carbonyl]-benzensulfonamide (glycopyramide); glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; and tolylcyclamide, or, if appropriate, in each case a pharmaceutically acceptable salt thereof.

Insulin secretion enhancers furthermore include the representatives of the new generation of SUs such as calcium (2S)-2-benzyl-3-(cis-hexahydro-2-isoindolinlycarbonyl)-propionate dihydrate (KAD-1229) and glimepiride (Hoe 490); and in free or pharmaceutically acceptable salt form.

Insulin secretion enhancers likewise include DPP-IV inhibitors, GLP1 and GLP1 agonists.

DPP-IV is a serine protease and catalyses cleavage of N-terminal Xaa-Pro or XaaAla dipeptide residues omcluding glucagon-like protein-1 (GLP-1). Corresponding inhibitors of DPP-IV increase circulating concentrations of GLP-1 and therefore increasing insulin secretion.

Representatives of DPP-IV inhibitors are described in WO98/19998 and WO00/34241. Preferred is 1-{2-[(5-cyanopyridin-2-yl)amino]ethylamino}acetyl-2(S)-cyanopyrrolidine dihydrochloride (cf. example 3 of WO98/19998) and (S)1-[(3-hydroxy-1-adamantyl)amino]-acetyl-2-cyanopyrrolidine (cf. example 1 of W00/34241).

GLP-1 and GLP-1 agonists likewise enhance insulin secretion.

A preferred insulin secretion enhancer is repaglinide and metformin, most preferred is nateglinide.

An insulin sensitivity enhancer restores impaired insulin receptor function to reduce insulin resistance and consequently enhance the insulin sensitivity.

An appropriate insulin sensitivity enhancer is, for example, an appropriate hypoglycemic thiazolidinedione derivative (glitazone).

An appropriate glitazone is, for example, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methylcyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297). Preferred are pioglitazone, rosiglitazone and troglitazone.

The structure of the active agents identified by generic or tradenames may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

Favorable effects can be verified that confirm that hypoglycemic agents such as insulin enhancers can restore early phase insulin secretion and reduce post-prandial glucose levels in subjects with IGM. A multi-center, double-blind, parallel group, randomized study can be conducted in subjects with IGM in order to evaluate the incidence of confirmed hypoglycemia and the effects on prandial glucose associated with the administration of nateglinide 30 mg, 60 mg or 120 mg or placebo before each main meal during 8 weeks of treatment. Subjects are selected on the basis of a 2-hour plasma glucose value after a 75 g oral glucose tolerance test (OGTT) and patients essentially meeting the following additional inclusion criteria are included in the study:

- two-hour glycemia post-OGTT between 7.8 to 11.1 mmol/L (one OGTT to be performed during the year before entering the study, the second to be performed within two weeks prior entering the study);
- FPG<7 mmol/L;
- patients are to have a body mass index (BMI) between 20–32 kg/m2;
- patients are to maintain prior diet during the full course of study;
- males, non-fertile females, females of child-bearing potential using a medically approved birth control method are included;
- the use of other antidiabetics during the trial is not permitted.

Corresponding dosages of e.g. nateglinide are administered with a large glass of water 2 (BID), 3 (TID) or 4 (QID) times daily depending on the number of main meals (breakfast, lunch, snack, dinner). The first dose is to be given with the first main meal (standardized meal i.e. 55% carbohydrates, 25% fat and 20% protein). Visits are scheduled to be performed at weeks 0, 2, 4 and 8 and the patients are to be fasted for at least 7 hours. All blood samples for laboratory evaluations are drawn between 07.00 and 10.00 a.m. HbA1c is to be measured at baseline and after 8 weeks of treatment (fasting glucose and fructosamine). Samples of blood are to be drawn at 10, 20, 20, 60, 120, and 180 minutes after drug administration (time 0) and the glucose and insulin levels to be measured. At weeks 0 and 8 visits, patients complete a standard meal challenge containing approximately 500 kcal and measurements of insulin and glucose will be performed.

The findings from analyses of all obtained data in such a study clearly revealed that 2 hour prandial glucose levels, HBA1c and fructosamine levels were surprisingly and significantly reduced, that early phase insulin secretion was restored, and that nateglinlde could prevent or delay the progression to type 2 diabetes mellitus. With longer treatment and follow-up, conditions and diseases associated with IGM could be prevented or reduced.

This type of study in individuals with IGM and particularly IFG and IGT differs from those in diabetics since the subjects have normal FPG and are nondiabetics or pre-diabetics.

Surprisingly, hypoglycemic agents as well as a combination of hypoglycemic agents can be used in subjects with IGM, especially IFG and/or IGT, for the prevention or delay of progression to overt diabetes mellitus type 2; for the prevention, reduction or delay in onset of a condition selected from the group consisting of increased microvascular complications; increased cardiovascular morbidity; excess cerebrovascular diseases; increased cardiovascular mortality and sudden death; higher incidences and mortality rates of malignant neoplasms; and other metabolic disturbances that are associated with IGM.

Furthermore, hypoglycemic agents as well as a combination of hypoglycemic agents can be used in subjects with IGM, especially IFG and/or IGT, for the prevention, reduction or delay in onset of a condition selected from the group e.g. consisting of retinopathy, other ophthalmic complications of diabetes, nephropathy, neuropathy, peripheral angiopathy, peripheral angiopathy, gangrene, myocardial infarctions, coronary heart disease, atherosclerosis, other acute and subacute forms of coronary ischemia, stroke, dyslipidemia, hyperuricemia, hypertension, angina pectoris, microangiopathic changes that result in amputation, cancer, cancer deaths, obesity, uricemia, insulin resistance, arterial occlusive disease, and atherosclerosis.

According to the present invention, hypoglycemic agents can be used in subjects with IGM, especially with IFG and/or IGT, to prevent or delay the progression to overt diabetes, to reduce microvascular complications of diabetes, to reduce vascular, especially cardiovascular, mortality and morbidity, especially cardiovascular morbidity and mortality, and to reduce increased mortality related to cancer in individuals with IGT.

Accordingly, the present invention relates to a method in subjects with IGM, especially IFG and/or IGT, for the prevention or delay of progression to overt diabetes mellitus type 2; for the prevention, reduction or delay in onset of a condition selected from the group consisting of increased microvascular complications; increased cardiovascular morbidity; excess cerebrovascular diseases; increased cardiovascular mortality and sudden death; higher incidences and mortality rates of malignant neoplasms; and other metabolic disturbances that are associated with IGM.

Especially, the present invention relates to a method used in subjects with IGM, especially IFG and/or IGT, for the prevention, reduction or delay in onset of a condition selected from the group e.g. consisting of retinopathy, other ophthalmic complications of diabetes, nephropathy, neuropathy, peripheral angiopathy, peripheral angiopathy gangrene, myocardial infarctions, coronary heart disease, atherosclerosis, other acute and subacute forms of coronary ischemia, stroke, dyslipidemia, hyperuricemia, hypertension, angina pectoris, microangiopathic changes that result in amputation, cancer, cancer deaths, obesity, uricemia, insulin resistance, arterial occlusive disease, and atherosclerosis.

Accordingly, the present invention relates to a method of prevention or delay of the progression to overt diabetes, especially type 2 (ICD-9 Code 250.2), prevention or reduction of microvascular complications like retinopathy (ICD-9 code 250.5), neurophathy (ICD-9 code 250.6), nephropathy (ICD-9 code 250.4) and peripheral angiopathy or gangrene (ICD-9 code 250.7), later termed "microvascular complications" in subjects with IGM, especially IFG and IGT. Further the present invention relates to a method to prevent or reduce conditions of excessive cardiovascular morbidity (ICD-9 codes 410–414), e.g. myocardial infarction (ICD-9 code 410), arterial occlusive disease, atherosclerosis and other acute and subacute forms of coronary ischemia (ICD-9 code 411–414), later termed "cardiovascular morbidity"; to prevent, reduce, or delay the onset of excess cerebrovascular diseases like stroke (ICD-9 codes 430–438); to reduce increased cardiovascular mortality (ICD-9 codes 390–459) and sudden death (ICD-9 code 798.1); to prevent the development of cancer (ICD-9 codes 140–208) and to reduce cancer deaths, in each case, in subjects with IGM, especially IFG and IGT. The method further relates to a method of prevention or reduction of other metabolic disturbances that are associated with IGM including hyperglycemia (including isolated postprandial hyperglycemia), dyslipidemia (ICD-9 code 272), hyperuricemia (ICD-9 code 790.6) as well as hypertension (ICD-9 codes 401–404) and angina pectoris (ICD-9 code 413.9), in each case, in subjects with IGM, especially IFG and IGT.

The codes identified hereinbefore and herafter according to the International Classification of Diseases $9^{th}$ version and the corresponding definitions allocated thereto are herewith incorporated by reference and likewise form part of the present invention.

The induction by hypoglycemic agents, in particular of early phase secretion, is rapidly reversible and the reduction of postprandial glucose levels is favorable for prevention or treatment in this indication.

The method comprises administering to a subject in need thereof an effective amount of hypoglycemic agents such as an insulin secretion enhancer or a pharmaceutically acceptable salt thereof. A subject in need of such method is a warm-blooded animal including man.

The present invention also relates to a method to be used in subjects with IGM, and especially IFG and/or IGT, and associated diseases and conditions such as isolated prandial hyperglycemia, prevention or delay of the progression to overt diabetes, especially type 2, prevention, reduction, or delay the onset of microvascular complications, prevention or reduction of gangrene or microangiopathic changes that result in amputation, prevention or reduction of excessive cardiovascular morbidity and cardiovascular mortality, prevention of cancer and reduction of cancer deaths.

The present invention likewise relates to a method of treatment of conditions and diseases associated with IGM and especially IFG and/or IGT (including isolated prandial hyperglycemia) including obesity, increased age, diabetes during pregnancy, dyslipidemia, high blood pressure, uricemia, insulin resistance, arterial occlusive disease, atherosclerosis, retinopathy, nephropathy, angina pectoris, myocardial infarction, and stroke.

Preferably, said preventions should be effected in individuals with glucose levels in the ranges that have been proven in large epidemiologic studies to confer increased cardiovascular, microvascular and cancer risk. These levels include levels of plasma glucose $\geq 7.8$ mmol/L mmol/L after an OGTT or casual glucose evaluation and/or fasting plasma glucose in the IFG range (fasting plasma glucose between 6.1 and 7 mmol/l). As new epidemiologic data become available to lower the glycemic levels that are incontrovertibly linked to the above-mentioned risks, or as the international standards for defining the IGT and IFG risk groups are changed, the use of the invention is also warranted for treatment of the groups at risk.

The present invention also relates to a method to be used in subjects with IFG comprising administering to a subject in need thereof a therapeutically effective amount of a DPP-IV inhibitor.

The present invention relates to the use of a hypoglycemic agent or a pharmaceutically acceptable salt thereof for the manufacture of a medicament in subjects with IGM, especially IFG and/or IGT, for the prevention or delay of progression to overt diabetes mellitus type 2; for the prevention, reduction or delay in onset of a condition selected from the group consisting of increased microvascular complications; increased cardiovascular morbidity; excess cerebrovascular diseases; increased cardiovascular mortality and sudden death; higher incidences and mortality rates of malignant neoplasms; and other metabolic disturbances that are associated with IGM.

The present invention relates to the use of an insulin secretion enhancer or a pharmaceutically acceptable salt thereof for the manufacture of a medicament for the prevention or delay of the progression to overt diabetes, especially type 2, prevention or reduction of microvascular complications, prevention or reduction of excessive cardiovascular morbidity and cardiovascular mortality, prevention of cancer and reduction of cancer deaths.

The present invention relates to the use of an insulin secretion enhancer or a pharmaceutically acceptable salt for the manufacture of a medicament in subjects with IGM, and especially IFG and/or IGT, and associated diseases and conditions such as isolated prandial hyperglycemia for the following: prevention or delay of the progression to overt diabetes, especially type 2, prevention or reduction of microvascular complications, prevention or reduction of excessive cardiovascular morbidity and cardiovascular mortality, prevention of cancer and reduction of cancer deaths.

The present invention relates to a pharmaceutical composition in subjects with IGM, especially IFG and/or IGT, for the prevention or delay of progression to overt diabetes mellitus type 2; for the prevention, reduction or delay in onset of a condition selected from the group consisting of increased microvascular complications; increased cardiovascular morbidity; excess cerebrovascular diseases; increased cardiovascular mortality and sudden death; higher incidences and mortality rates of malignant neoplasms; and other metabolic disturbances that are associated with IGM; comprising a hypoglycemic agent or a pharmaceutically acceptable salt thereof and a pharmaceutically acceptable carrier.

The present invention relates to a pharmaceutical composition for the prevention or delay of the progression to overt diabetes, especially type 2, prevention or reduction of microvascular complications, prevention or reduction of excessive cardiovascular morbidity and cardiovascular mortality, prevention of cancer and reduction of cancer deaths, comprising an insulin secretion enhancers or a pharmaceutically acceptable salt thereof and a pharmaceutically acceptable carrier.

The present invention relates to a pharmaceutical composition in subjects with IGM, and especially IFG and/or IGT and associated diseases and conditions such as isolated prandial hyperglycemia for the following: prevention or delay of the progression to overt diabetes, especially type 2, prevention or reduction of microvascular complications, prevention or reduction of excessive cardiovascular morbidity and cardiovascular mortality, prevention of cancer and reduction of cancer deaths.

The corresponding active ingredient or a pharmaceutically acceptable salt thereof may also be used in form of a hydrate or include other solvents used for crystallization.

Furthermore, the present invention relates to the combination such as a combined preparation or pharmaceutical composition, respectively, comprising at least one insulin secretion enhancer and alt least one insulin sensitiser; or at least two insulin secretion enhancers; or at least two insulin sensitisers; to be used in subjects with IGM, especially IFG and/or IGT, for the prevention or delay of progression to overt diabetes mellitus type 2; for the prevention, reduction or delay in onset of a condition selected from the group consisting of increased microvascular complications; increased cardiovascular morbidity; excess cerebrovascular diseases; increased cardiovascular mortality and sudden death; higher incidences and mortality rates of malignant neoplasms; and other metabolic disturbances that are associated with IGM.

Further benefits when applying the combination of the present invention are that lower doses of the individual drugs to be combined according to the present invention can be used to reduce the dosage, for example, that the dosages need not only often be smaller but are also applied less frequently, or can be used in order to diminish the incidence of side effects. This is in accordance with the desires and requirements of the patients to be treated.

Preferably, the jointly therapeutically effective amounts of the active agents according to the combination of the present invention can be administered simultaneously or sequentially in any order, separately or in a fixed combination.

The term "therapeutically effective amount" shall mean that amount of a drug or combination that will elicit the biological or medical response needed to achieve the therapeutic effect as specified according to the present invention in the warm-blooded animal, including man. A "therapeutically effective amount" can be administered when administering a single hypoglycemic agent and also in both a fixed or free combination of hypoglycemic agents. A "jointly effective amount" in a combination according to the present invention shall also include a non-effective amount of at least one of the agents to be combined, if the overall effect can be achieved by the combined administration of the (fixed or free) combination.

The pharmaceutical composition according to the present invention as described hereinbefore and hereinafter may be used for simultaneous use or sequential use in any order, for separate use or as a fixed combination.

Preferred components for a combination according to the present invention preferably those that are designated as preferred hypoglycemic agents, that are most preferably selected from nateglinide, repaglinide, metformin, pioglitazone, rosiglitazone, troglitazone, 1-{2-[(5-cyanopyridin-2-yl)amino]ethylamino}acetyl-2(S)-cyano-pyrrolidine, and (S)1-[(3-hydroxy-1-adamantyl)amino]-acetyl-2-cyano-pyrrolidine, or, if appropriate, in each case, a pharmaceutically acceptable salt thereof.

In a variation thereof, the present invention likewise relates to a "kit-of-parts", for example, in the sense that the components to be combined according to the present invention can be dosed independently or by use of different fixed combinations with distinguished amounts of the components, i.e. simultaneously or at different time points. The parts of the kit of parts can then e.g. be administered simultaneously or chronologically staggered, that is at different time points and with equal or different time intervals for any part of the kit of parts. Preferably, the time intervals are chosen such that the effect on the treated disease or condition in the combined use of the parts is larger than the effect that would be obtained by use of only any one of the components.

The invention furthermore relates to a commercial package comprising the combination according to the present invention together with instructions for simultaneous, separate or sequential use.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

Pharmaceutically acceptable salts e.g. of nateglinide are, for example, salts formed with bases, namely cationic salts such as alkali and alkaline earth metal salts, as well as ammonium salts.

The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carries, especially suitable for enteral or parenteral application.

The novel pharmaceutical preparations contain, for example, from about 10% to about 100%, preferably 80%, preferably from about 20% to about 60%, of the active ingredient. Pharmaceutical preparations according to the invention for enteral or parenteral administration are, for example, those in unit dose forms, such as sugar-coated tablets, tablets, capsules or suppositories, and furthermore ampoules. These are prepared in a manner known per se, for example by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

The doses for hypoglycemic agents for use according to the present invention may, for example, be those that are being used for agents that have already been launched. For example, tablets of repaglinide in doses of 0.5 mg, 1 mg or 2 mg of the active ingredient or tablets of metformin in doses of 500 mg or 850 mg of the active ingredient may be taken Likewise these doses may also be used for the agents to be combined combination according to the present invention. A person skilled in the art is fully enabled, based on his knowledge, to determine the specific doses for the specific hypolipidemic agents whether taken alone or in combination.

Nateglinide (I) is preferably administered to the warm-blooded animal in a dosage in the range of about 5 to 1200, more preferably 25 to 800, mg/day, when the warm-blooded animal is a human of about 70 kg body weight. Preferred dosages contain 30 mg, 60 mg or 120 mg of nateglinde to be administered preferably before the main meals. Depending on the number of main meals the dose regimen are two times a day (BID) or three times a day (TID) or four times a day (QID).

The following Examples illustrate the invention described above; they are not, however, intended to limit the scope of the invention in any way.

EXAMPLE 1

Tablets of Nateglinide (I)

216,000 tablets, each which contain 120 mg of nateglinide (I) are prepared as follows:

| Composition: | nateglinide (I) | 12.960 kg |
|---|---|---|
| | lactose, NF | 30.564 kg |
| | microcrystalline cellulose, NF | 15.336 kg |
| | povidone, USP | 2.592 kg |
| | croscarmellose sodium, NF | 3.974 kg |
| | colloidal silicon dioxide, NF | 1.382 kg |
| | magnesium stearate, NF | 1.231 kg |
| | coating: opadry yellow | 1.944 kg |
| | purified water, USP* | Q.S. |

*removed during process

Preparation process:

The microcrystalline cellulose, povidone, part of the croscarmellose sodium, nateglinide (I) and lactose are mixed in a high shear mixer and afterwards granulated using purified water. The wet granules are dried in a fluid bed dryer and passed through a screen. The colloidal silicon dioxide and the rest of the croscarmellose sodium are mixed, passed through a screen and blended with the dried granules in a V-blender. The magnesium stearate is passed through a screen, blended with the blend from the V-blender and afterwards the total mixture is compressed to tablets. The opadry yellow is suspended in purified water and the tablets are coated with the coating suspension.

EXAMPLE 2

Galenic Formulation of Nateglinide (I) No. 1

| intra-granular: | |
|---|---|
| nateglinide (I) | 120 mg |
| lactose monohydrate | 283 mg |
| microcrystalline cellulose | 142 mg |
| povidone | 24 mg |
| croscarmellose sodium | 24 mg |
| extra-granular: | |
| magnesium stearate | 7 mg |
| opadry white | 20 mg |

EXAMPLE 3

Galenic Formulation of Nateglinide (I) No. 2

| intra-granular: | |
|---|---|
| nateglinide (I) | 120 mg |
| lactose monohydrate | 283 mg |
| microcrystalline cellulose | 142 mg |
| povidone | 24 mg |
| croscarmellose sodium | 24 mg |
| extra-granular: | |
| croscarmellose sodium | 12.8 mg |
| magnesium stearate | 11.4 mg |
| opadry white | 18.0 mg |
| colliodal silicon dioxide | 12.8 mg |

EXAMPLE 4

Tablets of Nateglinide 108,000 tablets, each which contain 120 mg of nateglinide are prepared as follows:

| Composition: | nateglinide | 12.960 kg |
|---|---|---|
| | lactose, NF | 30.564 kg |
| | microcrystalline cellulose, NF | 15.336 kg |
| | povidone, USP | 2.592 kg |
| | croscarmellose sodium, NF | 3.974 kg |
| | colloidal silicon dioxide, NF | 1.382 kg |
| | magnesium stearate, NF | 1.231 kg |
| | coating: opadry yellow | 1.944 kg |
| | purified water, USP* | Q.S. |

*removed during process

Preparation process:

The microcrystalline cellulose, povidone, a portion of the croscarmellose sodium, nateglinide and lactose are granulated in a collette gral granulator with the addition of purified water. The wet granules are dried in a fluid bed dryer and passed through a screen. The colloidal silicon dioxide and the rest of the croscarmellose sodium are mixed, passed through a screen and blended with the dried granules in a V-blender. The magnesium stearate is passed through a screen, blended with the blend from the V-blender and afterwards the total mixture is compressed to tablets. The opadry yellow is suspended in purified water and the tablets are coated with the coating suspension. Variants of this process include adding the colloidal silica and the remaining croscarmellose sodium to the second granulator load after drying, then screening together; and combining as many as 3 granulator/drier loads per batch.

EXAMPLE 5

Pharmaceutical Composition of Nateglinide (120 mg)

| nateglinide | 120 mg |
|---|---|
| lactose monohydrate | 283 mg |
| microcrystalline cellulose | 142 mg |
| Povidone | 24 mg |
| croscarmellose sodium | 36.8 mg |
| magnesium stearate | 11.4 mg |
| opadry yellow | 18.0 mg |
| colloidal silicon dioxide | 12.8 mg |

What is claimed is:

1. A method for treating or preventing conditions and diseases associated with IGT or IFG comprising administering a nateglinide agent or a pharmaceutically acceptable salt thereof to subjects in need thereof.

2. The method of claim 1 for the prevention or delay of progression to overt diabetes mellitus type 2; for the prevention, reduction or delay in onset of a condition selected from the group consisting of increased microvascular complications; increased cardiovascular morbidity; excess cerebrovascular diseases; increased cardiovascular mortality and sudden death; higher incidences and mortality rates of malignant neoplasms; and other metabolic disturbances that are associated with IGM.

3. The method of claim 1 for the treatment of diseases and conditions associated with isolated prandial hyperglycemia and/or IFG.

4. The method of claim 1 for the prevention of conditions or diseases associated with IGT in subjects with prandial glucose excursions having 2 hour plasma glucose values between 7.8 to 11.1 mmol/L after an OGTT or casual glucose test.

5. The method of claim 3 wherein the diseases and conditions associated with isolated prandial hyperglycemia and/or IFG are selected from the group consisting of obesity, increased age, family history of diabetes, diabetes during pregnancy, dyslipidemia, high blood pressure, uricemia, insulin resistance, arterial occlusive disease, atherosclerosis, retinopathy, nephropathy, angina pectoris, myocardial infarction, and stroke.

* * * * *